United States Patent
Dumitru et al.

(10) Patent No.: US 9,863,903 B2
(45) Date of Patent: Jan. 9, 2018

(54) CONDENSATION SENSOR SYSTEMS AND METHODS

(71) Applicant: HONEYWELL ROMANIA SRL, Morris Plains, NJ (US)

(72) Inventors: Viorel G. Dumitru, Bucharest (RO); Stefan D. Costea, Bueharest (RO); Mihai Brezeanu, Bucharest (RO)

(73) Assignee: Honeywell International Inc., Morris Plains, NJ (US)

( * ) Notice: Subject to any disclaimer, the term of this patent is extended or adjusted under 35 U.S.C. 154(b) by 0 days.

(21) Appl. No.: 14/908,755

(22) PCT Filed: Aug. 1, 2013

(86) PCT No.: PCT/IB2013/056327
§ 371 (c)(1),
(2) Date: Jan. 29, 2016

(87) PCT Pub. No.: WO2015/015253
PCT Pub. Date: Feb. 5, 2015

(65) Prior Publication Data
US 2016/0161432 A1    Jun. 9, 2016

(51) Int. Cl.
*G01N 27/12* (2006.01)
*H01L 21/02* (2006.01)

(52) U.S. Cl.
CPC ........ *G01N 27/125* (2013.01); *G01N 27/121* (2013.01); *H01L 21/0254* (2013.01); *H01L 21/02631* (2013.01)

(58) Field of Classification Search
None
See application file for complete search history.

(56) References Cited

U.S. PATENT DOCUMENTS

| | | | |
|---|---|---|---|
| 5,644,501 A * | 7/1997 | Lin | G01N 27/286 204/400 |
| 2002/0078881 A1* | 6/2002 | Cuomo | C23C 14/0063 117/84 |
| 2010/0012987 A1* | 1/2010 | Yeh | G01N 27/414 257/253 |
| 2011/0108815 A1* | 5/2011 | Kummell | H01L 51/0016 257/40 |
| 2012/0107948 A1* | 5/2012 | Li | B82Y 15/00 436/149 |
| 2013/0111977 A1* | 5/2013 | Offermans | G01N 33/0009 73/31.06 |
| 2013/0276544 A1* | 10/2013 | Potasek | B81B 7/0048 73/715 |

* cited by examiner

*Primary Examiner* — Alexander Ghyka
(74) *Attorney, Agent, or Firm* — Brooks, Cameron & Huebsch, PLLC

(57) ABSTRACT

Condensation sensor systems and methods are described herein. Methods for forming a condensation sensor can include depositing a III-nitride on a substrate via sputtering, and implementing conductive contacts on the deposited III-nitride via a shadow mask.

20 Claims, 5 Drawing Sheets

CONDENSATION SENSOR SYSTEMS AND METHODS

TECHNICAL FIELD

The present disclosure relates to condensation sensor systems and methods.

BACKGROUND

Condensation sensors can be utilized in a number of applications. For example, condensation sensors can be utilized in heating, ventilation, and air conditioning (HVAC) systems. Condensation sensors can be utilized to determine a likely-hood of excessive condensation (e.g., indoor rain, etc.). In some systems the excessive condensation can cause damage to objects and/or equipment. Condensation sensors can be used to preempt excessive condensation by alerting a user that excessive condensation is likely to occur.

DETAILED DESCRIPTION

Methods of forming a condensation sensor can include depositing a III-nitride material on a substrate via sputtering and implementing conductive contacts on the deposited III-nitride material via a shadow mask. The III-nitride material can include Gallium Nitride (GaN), Aluminum Nitride (AlN), Indium nitride (InN), and/or the alloys of III-nitrides. The III-nitride material can interact with a substance having a polar molecule (e.g., water, etc.). The substance can interact with the III-nitride by creating a surface electron depletion region within the III-nitride material while a current is passing through the III-nitride material.

The surface electron depletion of the III-nitride material can decrease a current flowing between a number of conductive contacts and a computing device can determine a concentration of condensation and/or humidity based on the decreased current. A signal can be determined by the computing device. The signal can include: a quantity of condensation that is occurring on the III-nitride material, an alert of condensation occurring, and/or related information determined by the condensation sensor.

As will be appreciated, elements shown in the various embodiments herein can be added, exchanged, combined, and/or eliminated so as to provide a number of additional embodiments of the present disclosure. The proportion and the relative scale of the elements provided in the figures are intended to illustrate the embodiments of the present disclosure, and should not be taken in a limiting sense.

As used herein, "a" or "a number of" something can refer to one or more such things. For example, "a number of optical devices" can refer to one or more optical devices.

Figure 1:
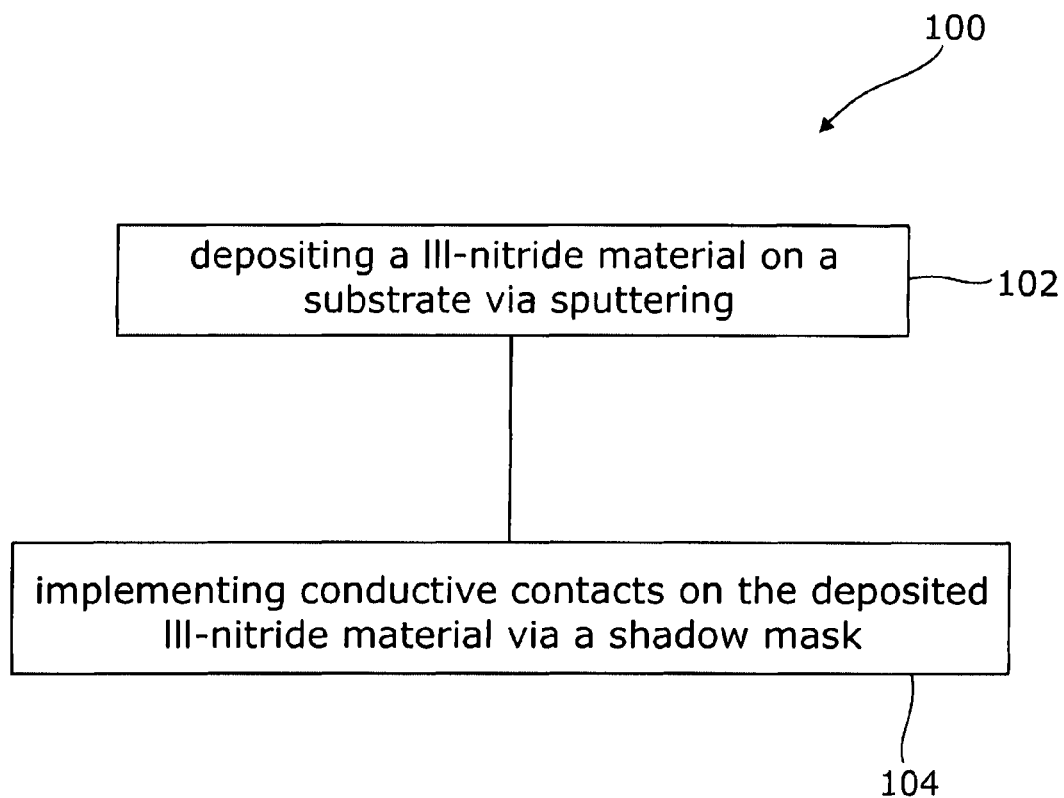
FIG. 1 illustrates an example method of forming a condensation sensor in accordance with one or more embodiments of the present disclosure.

FIG. 1 illustrates an example method 100 of forming a condensation sensor in accordance with one or more embodiments of the present disclosure. The method 100 can be utilized to form a condensation sensor and provide information related to the condensation of a substance having a polar molecule (e.g., water). The substance can interact with the condensation sensor and create a surface electron depletion that can induce a decrease in a flowing current that can be utilized by a computing device for analysis.

At box 102 the method can include depositing a III-nitride material on a substrate via sputtering. The III-nitride material can include Gallium Nitride (GaN), Aluminum Nitride (AlN), Indium nitride (InN), and/or the alloys of a III-nitride. The III-nitride material can be deposited on a substrate utilizing a physical vapor deposition (PVD). The physical vapor deposition (PVD) method of depositing a film of material can include sputter deposition (e.g., sputtering). For example, sputter deposition can be utilized to deposit a relatively thin layer of InN on the substrate. The layer of III-nitride material can be between few tens of nanometers and up to a few microns thick. For example, the layer of III-nitride can be approximately 1.8 microns thick.

The substrate can include silicon wafers, sapphire wafers, silicon carbide wafers, etc. The substrate can include also low cost, large area substrates such as glass material and plastic materials. The substrate can also include a flexible material such as a flexible plastic material. Depositing the III-nitride material via sputtering on a large area, low cost substrate material such as glass or plastic can significantly decrease the costs of manufacturing comparatively with other techniques such as metalorganic vapour phase epitaxy (MOCVD) or molecular beam epitaxy (MBE) typically used for producing III-nitrides based devices. Other techniques can use expansive sapphire, silicon carbide or silicon wafers. In addition, depositing the III-nitride material via sputtering (a low temperature process) allows the realization of sensors on flexible plastic substrates. Such flexible sensors can be very advantageous to use by applying or integrating into various non-planar surfaces (such as windshields, tubes, clothes, textiles, etc).

At box 104 the method can include implementing conductive contacts on the deposited III-nitride material via a shadow mask. Implementing conductive contacts on the deposited III-nitride material can include utilizing a shadow mask to deposit a conductive material (e.g., aluminum (Al), etc.) on the III-nitride. The deposited conductive material can act as contacts that can couple the condensation sensor to a computing device. The conductive contacts can be deposited in a number of locations on the deposited III-nitride material.

The conductive contacts can enable a computing device to determine a relative humidity within an area surrounding the deposited III-nitride material that is located between the conductive contacts. For example, the III-nitride material can be deposited on a flexible substrate and placed within a room. The conductive contacts can enable a computing device to determine the relative humidity within the room by determining condensation levels on the III-nitride material between the conductive contacts.

The conductive contacts can be used to apply a voltage across the deposited III-nitride. For example, the conductive contacts can be used to apply a voltage from a first position of the deposited III-nitride material to a second position of the deposited III-nitride material. In such a case, a current will flow from the first contact on the deposited III-nitride material to the second contact on the deposited III-nitride material. For example, a voltage can be applied between the two conductive contacts and based on the level of current flowing between the contacts a determination of humidity and/or condensation can be performed.

As described herein, a substance can interact with the III-nitride material and produce surface electron depletion within the III-nitride layer. The surface electron depletion can have an effect on the current flowing between the two conductive contacts. A computing device can determine a change in current from the situation when the substance is not present on the surface of the III-nitride material. The computing device can utilize the change in current to determine the humidity and/or condensation likelihood within an area.

The condensation sensor can act as an open gate thin film transistor. That is, the condensation sensor can include an electron accumulation layer that interacts with the substance. The interaction of the substance can deplete electrons from the electron accumulation layer and thus it can decrease the source-drain current of the transistor. For example, water droplets can condense on the III-nitride material and decrease the source-drain current of the transistor.

The decrease in current can be detected by a computing device and analyzed to determine a quantity of condensation and/or humidity of an area. In this example, when the water droplets evaporate there can be an increase in the source-drain current of the transistor and the computing device can determine a new quantity of condensation.

The condensation sensor can show a relatively rapid response time. For example, the response time can be approximately two seconds from a change in a quantity of condensation and/or humidity within an area. This is significantly better compared to previous condensation sensors that show response times ranging from five seconds to three minutes.

Figure 2:
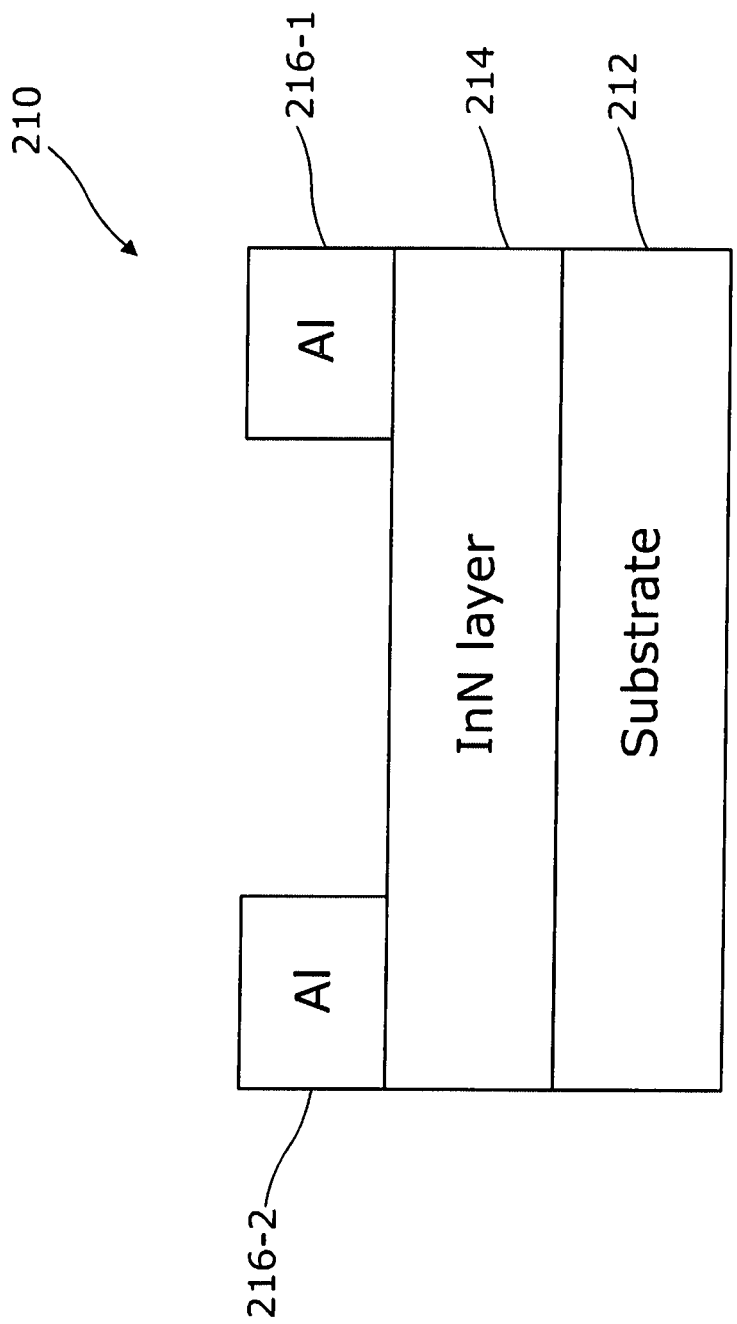
FIG. 2 illustrates an example of a condensation sensor in accordance with one or more embodiments of the present disclosure.

FIG. 2 illustrates an example of a condensation sensor 210 in accordance with one or more embodiments of the present disclosure. The condensation sensor 210 can include a III-nitride material deposited on a substrate material 212. As described herein, the III-nitride material can be InN. InN can include a number of properties including: a low band gap (e.g., an energy range in a solid material where no electron states can exist), relatively high electron mobility, piezoelectricity, surface electron accumulation, among other properties. The InN can be deposited as a single material and/or as an alloy with a different material such as GaN and/or AlN.

The III-nitride 214 material can be deposited at a number of thicknesses from few tens of nanometers and up to few microns. For example, InN can be deposited at measurements close or at 1.8 microns thick. As described herein, the III-nitride material can be deposited on a substrate 212 that is a flexible material utilizing sputter deposition. The flexible material can include a flexible plastic material.

The condensation sensor 210 can include a number of conductive contacts 216-1, 216-2. The conductive contacts 216-1, 216-2 can be placed at two different locations on the III-nitride material 214 between the two locations. The condensation sensor 210 can utilize a current that flows between a first conductive contact 216-1 and received at a second conductive contact 216-2. The decrease and/or increase in current from the first conductive contact 216-1 to the second conductive contact 216-2 can be utilized to determine a concentration of condensation on the III-nitride material 214 between the first conductive contact 216-1 and the second conductive contact 216-2.

The conductive contacts 216-1, 216-2 can be coupled to a computing device as described herein. The computing device can apply a voltage between the two contacts and determine the current flowing between the contacts.

Figure 3:
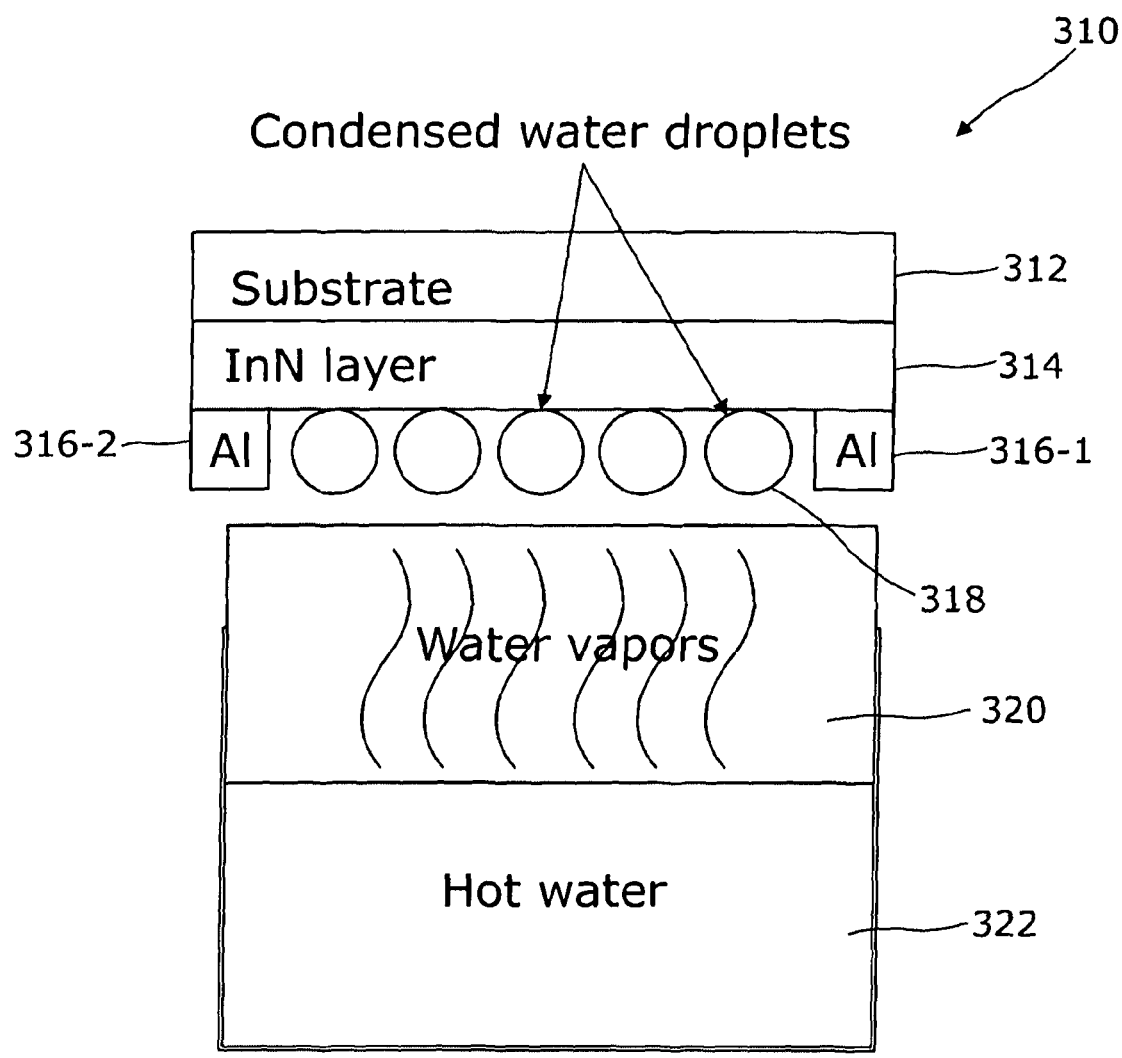
FIG. 3 illustrates an example of a condensation sensor in accordance with one or more embodiments of the present disclosure.

FIG. 3 illustrates an example of a condensation sensor 310 in accordance with one or more embodiments of the present disclosure. The condensation sensor 310 can include the same and/or similar features to the condensation sensor 210 as referenced in FIG. 2.

The condensation sensor 310 can be positioned over a source of water vapor and/or a location of possible condensation. FIG. 3 represents a condensation sensor 310 that is purposely placed over a container of hot water 322 that is producing water vapor 320. In this example the water vapor 320 can condense and form water droplets 318 on the III-nitride layer 314 that has been deposited on a substrate material 312. As described herein, the condensed water droplets can interact with the III-nitride layer and cause a change in current flowing between a first conductive contact 316-1 and a second conductive contact 316-2.

As described herein the conductive contacts 316-1, 316-2 can be coupled to a computing device that is capable of determining a current flowing from the first conductive contact 316-1 to the second conductive contact 316-2. The computing device can utilize a change in current to determine a concentration of water droplets 318 between the first conductive contact 316-1 and the second conductive contact 316-2. The change in current can include a decrease and/or increase in current by 20-30 percent.

Figure 4:
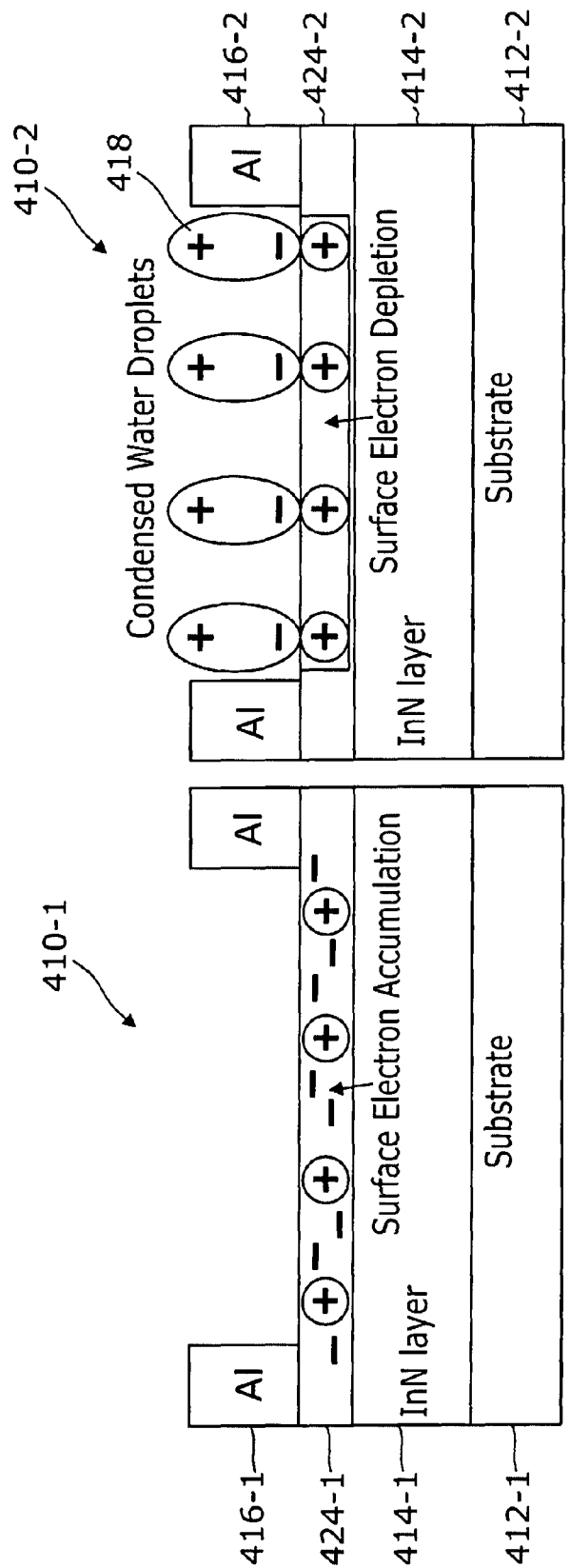
FIG. 4 illustrates an example of condensation sensors in accordance with one or more embodiments of the present disclosure.

FIG. 4 illustrates an example of condensation sensors 410-1, 410-2 in accordance with one or more embodiments of the present disclosure. The condensation sensor 410-1 can display a surface electron accumulation 424-1 when there is a relatively low amount (e.g., no condensation, etc.) of condensation interacting with the III-nitride material 414-1. In addition, the condensation sensor 410-2 can display a surface electron depletion 424-2 when a relatively high amount of condensation (e.g., detectable traces of condensation, etc.) is interacting with the III-nitride material 414-2.

The condensation sensors 410-1, 410-2 can include the same and/or similar features as condensation sensor 210 as referenced in FIG. 2 and condensation sensor 310 as referenced in FIG. 3. For example, the condensation sensors 410-1, 410-2 can include a III-nitride material 414-1, 414-2 deposited by a sputter deposition on a substrate 412-1, 412-2, wherein the substrate can be a flexible substrate as described herein. The condensation sensors 410-1, 410-2 can also include a number of conductive contacts 416-1, 416-2 with III-nitride between the number of conductive contacts 416-1, 416-2. As described herein, the conductive contacts 416-1, 416-2 can comprise a conductive material (e.g., Aluminum (Al), etc.) and can be coupled with a computing device.

Condensation sensor 410-1 can represent a condensation sensor that lacks water droplets (e.g., water droplets 418) on the III-nitride material 414-1. In the absence of water droplets on the III-nitride material 414-1 a surface electron accumulation 424-1 region exists on the III-nitride material 414-1.

Condensation sensor 410-2 can represent a condensation sensor with water droplets 418 that have condensed on the condensation sensor 410-2. The water droplets 418 can interact with surface electron accumulation 424-1 of the III-nitride material 414-2 and repeal electrons from the III-nitride material 414-2 causing a surface electron depletion 424-2. The surface electron depletion 424-2 can cause a decrease in the current flowing between conductive contacts 416-1, 416-2. The magnitude of the decrease in the flowing current can be utilized to determine a concentration of droplets condensed on the III-nitride material 414-2 and/or humidity of an area.

Figure 5:
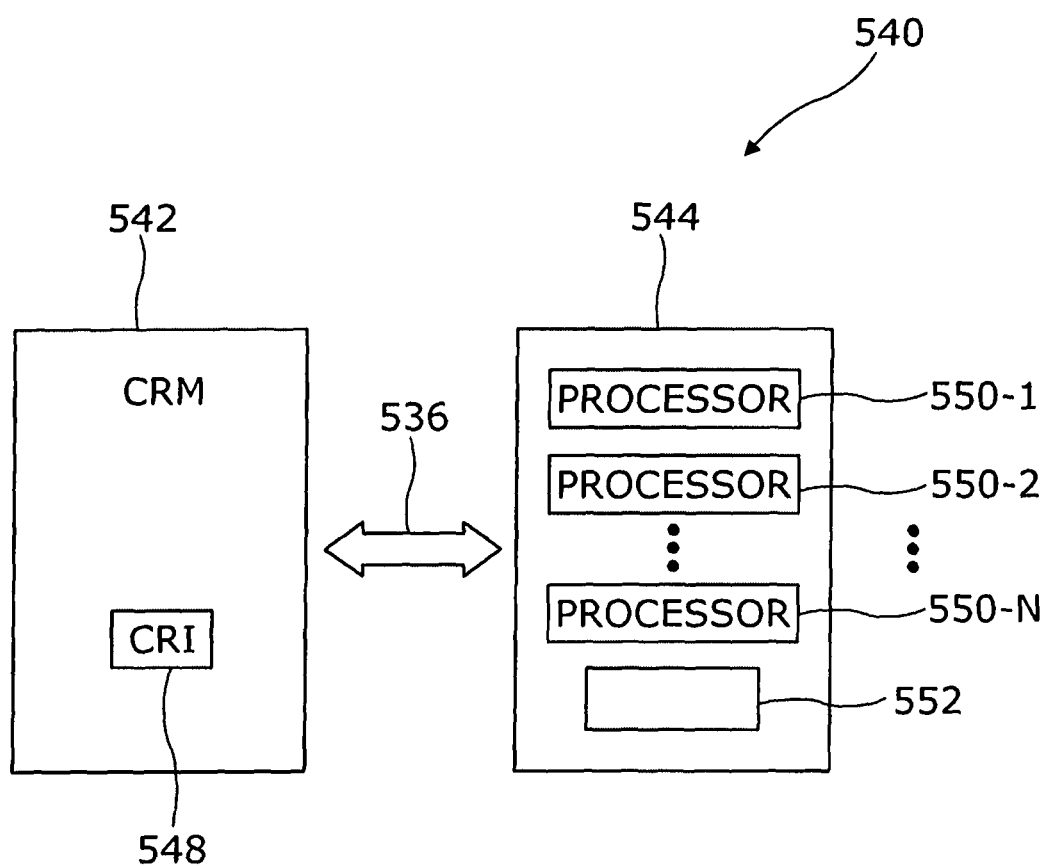
FIG. 5 illustrates a block diagram of an example of a computing device in accordance with one or more embodiments of the present disclosure.

FIG. 5 illustrates a block diagram of an example of a computing device 540 in accordance with one or more embodiments of the present disclosure. The computing device 540 can include a communication interface (e.g., wireless network interface controller, IEEE 802.11 adapters, etc.) for receiving wireless data. The communication interface can be integrated in the computing device 540 and/or be an external card.

The computing device 540, as described herein, can also include a computer readable medium (CRM) 542 in communication with processing resources 550-1, 550-2, . . . , 550-N. CRM 542 can be in communication with a device 544 (e.g., a Java® application server, among others) having processor resources 550-1, 550-2, . . . , 550-N. The device 544 can be in communication with a tangible non-transitory CRM 542 storing a set of computer-readable instructions (CRI) 548 (e.g., modules) executable by one or more of the processor resources 550-1, 550-2, . . . , 550-N, as described herein. The CRI 548 can also be stored in remote memory managed by a server and represent an installation package that can be downloaded, installed, and executed. The device 544 can include memory resources 552, and the processor resources 550-1, 550-2, . . . , 550-N can be coupled to the memory resources 552.

Processor resources 550-1, 550-2, . . . , 550-N can execute CRI 548 that can be stored on an internal or external non-transitory CRM 542. The processor resources 550-1, 550-2, . . . , 550-N can execute CRI 548 to perform various functions. For example, the processor resources 550-1, 550-2, . . . , 550-N can execute CRI 548 to perform a number of functions (e.g., applying a particular voltage, determining a return current, sensing condensation, sensing water condensation, etc.). A non-transitory CRM (e.g., CRM 542), as used herein, can include volatile and/or non-volatile memory. Volatile memory can include memory that depends upon power to store information, such as various types of dynamic random access memory (DRAM), among others. Non-volatile memory can include memory that does not depend upon power to store information. Examples of non-volatile memory can include solid state media such as flash memory, electrically erasable programmable read-only memory (EEPROM), phase change random access memory (PCRAM), magnetic memory such as a hard disk, tape drives, floppy disk, and/or tape memory, optical discs, digital versatile discs (DVD), Blu-ray discs (BD), compact discs (CD), and/or a solid state drive (SSD), as well as other types of computer-readable media.

The non-transitory CRM 542 can also include distributed storage media. For example, the CRM 542 can be distributed among various locations.

The non-transitory CRM 542 can be integral, or communicatively coupled, to a computing device, in a wired and/or a wireless manner. For example, the non-transitory CRM 542 can be an internal memory, a portable memory, a portable disk, or a memory associated with another computing resource (e.g., enabling CRI's to be transferred and/or executed across a network such as the Internet).

The CRM 542 can be in communication with the processor resources 550-1, 550-2, . . . , 550-N via a communication path 546. The communication path 546 can be local or remote to a machine (e.g., a computer) associated with the processor resources 550-1, 550-2, . . . , 550-N. Examples of a local communication path 546 can include an electrical bus internal to a machine (e.g., a computer) where the CRM 542 is one of volatile, non-volatile, fixed, and/or removable storage medium in communication with the processor resources 550-1, 550-2, . . . , 550-N via the electrical bus. Examples of such electrical buses can include Industry Standard Architecture (ISA), Peripheral Component Interconnect (PCI), Advanced Technology Attachment (ATA), Small Computer System Interface (SCSI), Universal Serial Bus (USB), among other types of electrical buses and variants thereof.

The communication path 546 can be such that the CRM 542 is remote from the processor resources e.g., 550-1, 550-2, . . . , 550-N, such as in a network relationship between the CRM 542 and the processor resources (e.g., 550-1, 550-2, . . . , 550-N). That is, the communication path 546 can be a network relationship. Examples of such a network relationship can include a local area network (LAN), wide area network (WAN), personal area network (PAN), and the Internet, among others. In such examples, the CRM 542 can be associated with a first computing device and the processor resources 550-1, 550-2, . . . , 550-N can be associated with a second computing device (e.g., a Java® server).

As described herein, a "module" can include computer readable instructions (e.g., CRI 548) that can be executed by a processor to perform a particular function. A module can also include hardware, firmware, and/or logic that can perform a particular function.

As used herein, "logic" is an alternative or additional processing resource to execute the actions and/or functions, described herein, which includes hardware (e.g., various forms of transistor logic, application specific integrated circuits (ASICs)), as opposed to computer executable instructions (e.g., software, firmware) stored in memory and executable by a processor.

Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the disclosure.

It is to be understood that the above description has been made in an illustrative fashion, and not a restrictive one. Combination of the above embodiments, and other embodiments not specifically described herein will be apparent to those of skill in the art upon reviewing the above description.

The scope of the various embodiments of the disclosure includes any other applications in which the above structures and methods are used. Therefore, the scope of various embodiments of the disclosure should be determined with reference to the appended claims, along with the full range of equivalents to which such claims are entitled.

In the foregoing Detailed Description, various features are grouped together in example embodiments illustrated in the figures for the purpose of streamlining the disclosure. This method of disclosure is not to be interpreted as reflecting an intention that the embodiments of the disclosure require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

What is claimed:

1. A method for forming a condensation sensor, comprising:
   sputtering a III-nitride material 1.8 microns thick on a non-planar flexible substrate to form an electron accumulation layer that is accessible for contact with a polar substance and when the polar substance interacts with the electron accumulation layer the polar substance depletes electrons from the electron accumulation layer, wherein the electron accumulation layer is an open gate transistor;
   implementing conductive contacts on the deposited III-nitride material at a first location and a second location via a shadow mask; and
   coupling the conductive contacts to a computing device to apply a voltage across the deposited III-nitride material from a first conductive contact at the first location to a second conductive contact at the second location, wherein the computing device determines a relative humidity of an area based on an altered current flowing between the first conductive contact and the second conductive contact caused by the polar substance.

2. The method of claim 1, wherein depositing a III-nitride material on a substrate includes depositing an indium nitride material.

3. The method of claim 1, wherein depositing a III-nitride material includes depositing the III-nitride material on a flexible substrate.

4. The method of claim 3, wherein depositing a III-nitride material on a flexible substrate includes depositing the III-nitride material on a plastic material.

5. The method of claim 1, wherein depositing a III-nitride material on a substrate includes depositing the III-nitride material on a glass substrate material.

6. The method of claim 1, wherein depositing a III-nitride material on a substrate includes depositing the III-nitride material on a substrate in a wafer form.

7. The method of claim 6, wherein depositing a III-nitride material on a substrate in a wafer form includes depositing the III-nitride material on the wafer form comprising one of:
   a silicon wafer;
   a sapphire wafer; and
   a carbide wafer.

8. A method for forming a condensation sensor, comprising:
   sputtering a III-nitride material 1.8 microns thick on a non-planar flexible substrate to form an electron accumulation layer that is accessible for contact with a polar substance and when the polar substance interacts with the electron accumulation layer the polar substance depletes electrons from the electron accumulation layer, wherein the electron accumulation layer is an open gate transistor;
   implementing conductive contacts on the deposited III-nitride material at a first location and a second location via a shadow mask; and
   coupling the conductive contacts to a computing device to apply a voltage across the deposited III-nitride material from a first conductive contact at the first location to a second conductive contact, at the second location, wherein the computing device determines a current passing through the deposited III-nitride material and a relative humidity of an area based on the current flowing between the conductive contacts caused by the polar substance.

9. The method of claim 8, comprising determining a humidity based on the current passing through the deposited III-nitride material.

10. The method of claim 8, wherein determining the current includes determining the current passing through the deposited III-nitride material between the conductive contacts.

11. The method of claim 8, comprising determining a condensation concentration based on the determined current.

12. The method of claim 8, comprising applying a voltage to one of the conductive contacts.

13. The method of claim 8, wherein implementing the conductive contacts includes coupling the conductive contacts to a computing device.

14. The method of claim 8, wherein sputtering includes a physical vapor deposition of the III-nitride material.

15. The method of claim 8, wherein depositing the III-nitride material includes depositing the III-nitride material at 1.8 microns thick.

16. A condensation sensor, comprising:
    a layer of III-nitride material 1.8 microns thick on a non-planar flexible substrate that forms an electron accumulation layer that is accessible for contact with a polar substance and wherein when a polar substance interacts with the layer the substance depletes electrons from the electron accumulation layer, wherein the electron accumulation layer is an open gate transistor;
    a number of conductive contacts coupled to the deposited III-nitride material via a shadow mask; and
    a computing device coupled to the number of conductive contacts to apply a voltage across the deposited III-nitride material from a first conductive contact to a second conductive contact, wherein the computing device determines a relative humidity of an area based on an altered current flowing between the first conductive contact and the second conductive contact caused by the polar substance.

17. The condensation sensor of claim 16, wherein a surface electron accumulation is displayed on the III-nitride material when no detectable trace of condensation is interacting with the III-nitride material.

18. The condensation sensor of claim 16, wherein a surface electron depletion is displayed on the III-nitride material when a detectable trace of condensation is interacting with the III-nitride material.

19. The condensation sensor of claim 16, wherein the substrate is a flexible substrate.

20. The condensation sensor of claim 16, wherein the computing device provides and measures a current between the number of conductive contacts.

* * * * *